(12) United States Patent
Shifrin et al.

(10) Patent No.: US 8,042,720 B2
(45) Date of Patent: Oct. 25, 2011

(54) DEVICE FOR AFFIXING OF TUBULAR MEDICAL ACCESSORY TO A BODY PASSAGE

(75) Inventors: Edward G. Shifrin, Raanana (IL); Mordehi D. Shvartsman, Haifa (IL); Mark A. Umansky, Haifa (IL); Ralk Kolvenbach, Dusseldorf (DE)

(73) Assignee: ES Vascular Ltd., Haifa Bay (IL)

( * ) Notice: Subject to any disclaimer, the term of this patent is extended or adjusted under 35 U.S.C. 154(b) by 604 days.

(21) Appl. No.: 12/074,633

(22) Filed: Mar. 4, 2008

(65) Prior Publication Data
US 2008/0243223 A1 Oct. 2, 2008

Related U.S. Application Data

(60) Provisional application No. 60/908,787, filed on Mar. 29, 2007.

(51) Int. Cl.
*A61B 17/068* (2006.01)

(52) U.S. Cl. ............ 227/179.1; 227/175.1; 227/19; 606/108; 606/198

(58) Field of Classification Search ........... 227/179.1, 227/19, 175.1
See application file for complete search history.

(56) References Cited

U.S. PATENT DOCUMENTS

| | | | |
|---|---|---|---|
| 4,773,131 A * | 9/1988 | Koza .................... 24/459 |
| 5,346,115 A * | 9/1994 | Perouse et al. .......... 227/179.1 |
| 5,443,477 A | 8/1995 | Marin et al. |
| 5,507,769 A | 4/1996 | Marin et al. |
| 5,591,196 A | 1/1997 | Marin et al. |
| 5,618,300 A | 4/1997 | Marin et al. |
| 5,695,517 A | 12/1997 | Marin et al. |
| 5,713,907 A * | 2/1998 | Hogendijk et al. ......... 606/108 |
| 5,713,917 A * | 2/1998 | Leonhardt et al. ......... 606/194 |
| 5,968,053 A * | 10/1999 | Revelas ................ 606/108 |
| 6,039,749 A | 3/2000 | Marin et al. |

(Continued)

FOREIGN PATENT DOCUMENTS
EP 1290989 3/2003
(Continued)

OTHER PUBLICATIONS

International Search Report for PCT/IL2008/00279, mailed on Jul. 10, 2008, 2 pages.

*Primary Examiner* — Lindsay Low
(74) *Attorney, Agent, or Firm* — Mintz, Levin, Cohn, Ferris, Glovsky & Popeo, P.C.

(57) ABSTRACT

A device for affixing a tubular medical accessory to a wall of a body passage is disclosed. The said device comprises a handle portion, a barrel portion and a working head portion, said barrel portion is fitted with a pushing rod displaceable along the barrel portion upon actuating the handle portion. The working head portion is fitted with a plurality of wings and levers and said wings are preloaded with a plurality of staples. Upon initial displacement of the pushing rod in a distal direction the wings are swiveled towards the medical accessory such that they abut it and stretch it together with the body passage in a radial direction. Upon still further displacement of the pushing rod the levers are swiveled and cause the staples to exit from the wings such that the staples pierce the accessory and the wall of the body passage and affix the accessory to the body passage.

13 Claims, 4 Drawing Sheets

U.S. PATENT DOCUMENTS

| | | |
|---|---|---|
| 6,168,610 B1 | 1/2001 | Marin et al. |
| 6,217,585 B1 * | 4/2001 | Houser et al. ............... 606/108 |
| 6,290,674 B1 * | 9/2001 | Roue et al. .................. 604/107 |
| 6,336,933 B1 | 1/2002 | Parodi |
| 6,561,969 B2 * | 5/2003 | Frazier et al. ................. 600/16 |
| 6,575,994 B1 | 6/2003 | Marin et al. |
| 6,592,593 B1 | 7/2003 | Parodi et al. |
| 6,726,697 B2 * | 4/2004 | Nicholas et al. ............. 606/153 |
| 6,743,247 B1 * | 6/2004 | Levinson et al. ............ 606/200 |
| 7,125,412 B2 | 10/2006 | Shifrin et al. |
| 7,351,258 B2 * | 4/2008 | Ricotta et al. ............... 623/1.36 |
| 7,549,983 B2 | 6/2009 | Roue et al. .................. 604/500 |
| 7,637,932 B2 | 12/2009 | Bolduc et al. ............... 623/1.11 |
| 7,699,864 B2 | 4/2010 | Kick et al. .................. 606/198 |
| 2001/0044656 A1 * | 11/2001 | Williamson et al. ......... 623/2.11 |
| 2002/0177862 A1 | 11/2002 | Aranyi et al. |
| 2003/0023248 A1 | 1/2003 | Parodi |
| 2003/0149441 A1 * | 8/2003 | Shifrin et al. ................ 606/153 |
| 2005/0209685 A1 * | 9/2005 | Shifrin et al. ................ 623/1.23 |
| 2006/0289601 A1 | 12/2006 | Orban, III |
| 2009/0240262 A1 * | 9/2009 | Shifrin et al. ................ 606/139 |

FOREIGN PATENT DOCUMENTS

| | | |
|---|---|---|
| EP | 1308131 A1 | 5/2003 |
| WO | WO 95/21593 | 9/1995 |
| WO | WO 96/11648 | 4/1996 |
| WO | WO 00/16701 | 3/2000 |
| WO | WO 00/64357 | 11/2000 |
| WO | WO 02/00122 | 1/2002 |
| WO | WO 2005/089059 | 9/2005 |
| WO | WO 2005089059 A2 * | 9/2005 |
| WO | WO 2006/081174 | 8/2006 |
| WO | WO 2006/082574 | 8/2006 |

* cited by examiner

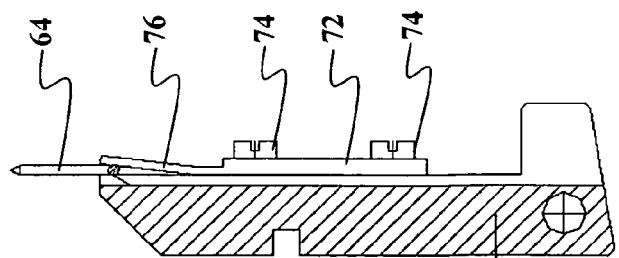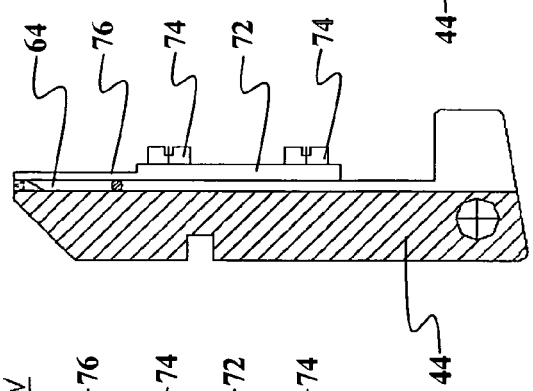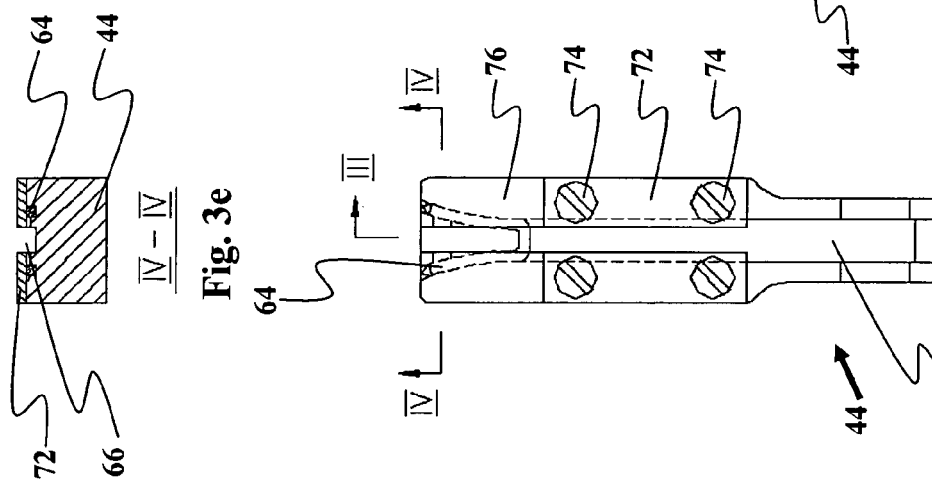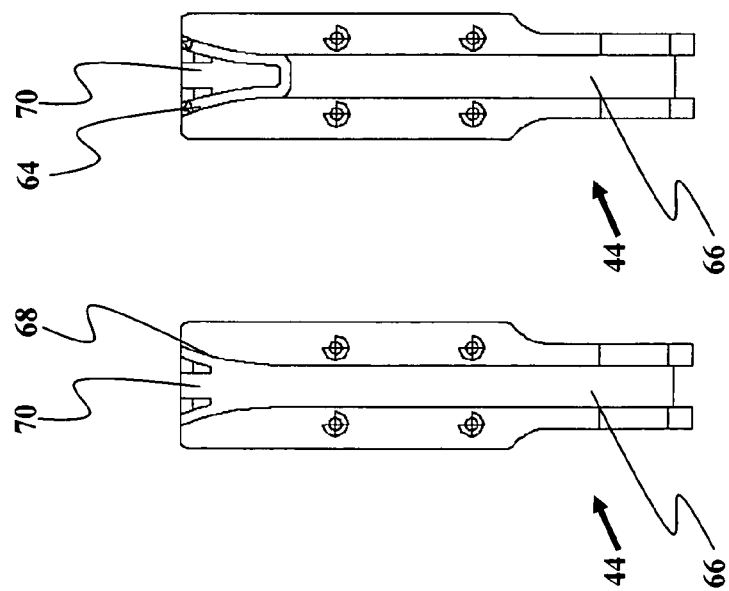

DEVICE FOR AFFIXING OF TUBULAR MEDICAL ACCESSORY TO A BODY PASSAGE

CROSS-REFERENCE TO RELATED APPLICATIONS

The present application claims priority to U.S. Provisional Application No. 60/908,787, filed Mar. 29, 2007, and entitled "Apparatus for Fixation of Stent-Grafts to Inner Wall of a Vessel" and incorporates its entire disclosure hereby reference.

FIELD OF THE INVENTION

The present invention generally refers to medicine, in particular to vascular surgeries during which prosthesis is introduced into a vessel and secured at the vessel wall.

More specifically the present invention refers to devices and methods used in surgical operations associated with aortic surgery for treating of aneurysm by inserting stent-graft to the damaged aorta. Even more specifically the invention refers to affixing stent-grafts for treating abdominal aortic aneurysm when the stent-graft is brought into aorta through peripheral arteries without opening the abdominal and thoracic cavities.

It should be borne in mind however that the present invention is not limited strictly to affixing of stent-graft to aorta while treating the abdominal aortic aneurism. The present invention can be used also for affixing of other tubular medical accessories within arteries or veins or within any other hollow body passage or cavity. An example of such application would be affixing of aortic trans catheter heart valves.

DESCRIPTION OF PRIOR ART

There are known in the art surgical devices for affixing prosthesis to the internal wall of a body lumen. For example J. Parodi discloses in U.S. Pat. No. 6,336,933, EP 1308131 A1 and US Pat. Appl. 2003/0023248 systems and methods for securing a single stitch inside vascular lumen.

In U.S. Pat. No. 6,592,593 and in WO 00/16701 J. Parodi discloses an applicator, which can be set up inside a vessel for affixing prosthesis to the vessel wall. In US Pat. Appl. 2002/0177862 and WO 00/64357 E. Arany with a co-inventor disclose a device for endovascular affixing of a prosthesis using at least one stapler. The device has a chamber loadable with additional staplers.

It should be appreciated that the known methods and systems for delivery and affixing of endovascular prostheses usually employ two separate mechanical systems, which fulfill different tasks, i.e. a system which delivers the prosthesis into vessel and a separate system for affixing the prosthesis to the vessel.

The additional methods and devices based on this principle are disclosed in the following references: U.S. Pat. Nos. 5,443,477, 5,507,769, 5,591,196, 5,618,300, 5,695,517, 6,039,749, 6,168,610, 6,575,994, WO 95/21593, 96/11648, EP 1290989.

There is known in the art an apparatus disclosed in U.S. Pat. No. 7,125,412. This apparatus allows affixing prosthesis to the aorta wall with staples. The affixing is carried out upon inserting the apparatus in the aorta in the course of surgical operation during which an incision is cut in the aorta wall. Unfortunately this apparatus can be employed only in the course of such a surgical operation. Furthermore, this apparatus requires the use of an external support means for reliable securing the staple edges; otherwise neither in aorta nor in vessels having thin walls with thickness of 0.2-0.4 mm reliable securing of the prosthesis is possible.

Currently, the standard method of healing aneurysm is a surgical procedure, which is intended for restoring the affected, expanded section of the abdominal aorta. This surgical procedure is carried out with anesthesia and lasts about 3-4 hours. The aneurysm is accessed through an abdominal incision. Aneurismal dilated aorta section is removed and a synthetic prosthesis is stitched in instead. Usually after such surgery, the patient remains in intensive care unit for one day and then 8-14 additional days the patient spends at the clinic.

There also exists an alternative method of treatment of damaged vessels. This method is known as an "endovascular prosthesis procedure", whereby the endo-prosthesis (so-called stent-graft, which is woven polyester tube with reinforcing inner metallic frame) is placed into the damaged vessel, e.g. into aneurism. This method neither requires incision of the vessel nor the surrounding tissue. This method may be used in patients, for whom a surgical operation may be not recommended for any reason, as well as in patients who prefer not to go through a surgical operation. During the endovascular prosthesis procedure the stent-graft (endo-prosthesis) is used to strengthen the weak vessel wall and to prevent vessel's rupture. Endo-prosthesis is deployed into the vessel by a dedicated delivering catheter configured as a long, tube-like device adapted for bringing the endo-prosthesis in the vessel. Implanting of endo-prosthesis is carried out under local/epidural anesthesia or narcosis. To carry out the procedure only two small cuts are made at the upper part of each hip if the prosthesis is to be inserted in the aorta.

Endovascular prosthesis treatment is an efficient alternative in treating of large vessels like abdominal aortic aneurysm.

This method allows:
  to reduce or avoid narcosis and lung ventilation;
  to reduce or avoid damage of blood circulation in vital organs and in lower extremities;
  to reduce or avoid complications, which may occur after an open surgery;
  to reduce the hospitalization and rehabilitation time;
  to reduce loss of blood.

Unfortunately no simple device is available, which does not require auxiliary means and allows affixing the stent-graft reliably in the course of the endovascular prosthesis procedure.

SUMMARY OF THE INVENTION

The main object of the invention is providing a new and improved device and method for affixing intravascular stent-grafts to a damaged vessel without the necessity in surgical operation associated with opening cavities surrounding the damaged vessel.

Another object of the invention is providing a new and improved device for affixing stent-grafts brought in the damaged vessel by intravascular prosthesis procedure.

Still further object of the invention is providing a new and improved device and method for affixing stent-grafts during treatment of abdominal aortic aneurysm without opening of abdominal and thoracic cavities and thus reducing the chance of traumatism.

Another object of the invention is providing a new and improved device and method for fast affixing intravascular stent-grafts to a damaged vessel by bringing stent-grafts into damaged vessel through peripheral vessels.

Still further object of the invention is providing a new and improved device and method for simple, reliable and fast affixing stent-grafts to a damaged vessel without the necessity in external support or any other auxiliary means, as for example required in the apparatus disclosed in U.S. Pat. No. 7,125,412.

BRIEF DESCRIPTION OF THE DRAWINGS

FIGS. 3a and 3b are respective top views of a separator before loading the staple and with the staple loaded.

FIG. 3c is a top view of the wing with a resilient plank secured thereon.

FIG. 3d is cross-sectional view of FIG. 3c taken along section III-III with the staple loaded but not protruded yet.

FIG. 3e is cross-sectional view of FIG. 3c taken along section IV-IV.

FIG. 3f is cross-sectional view of FIG. 3c taken along section III-III showing the staple protruded.

DEVICE DESCRIPTION

Figure 1:
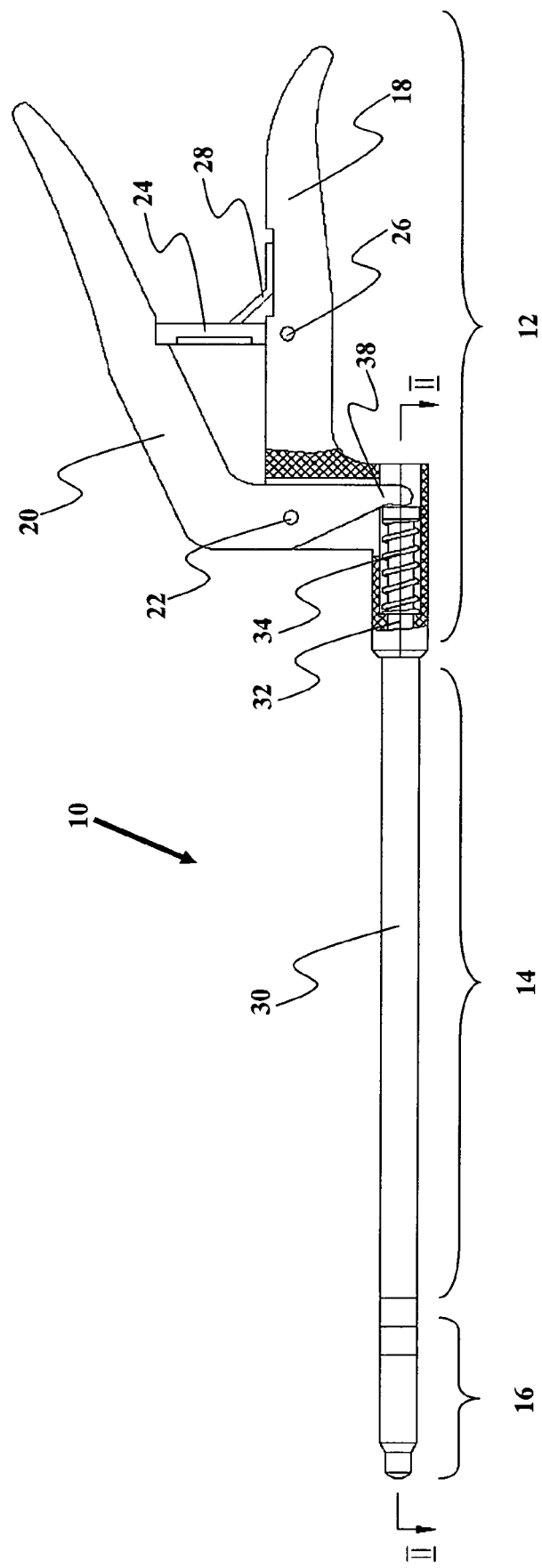
FIG. 1 is a side view of the device according to the present invention showing handle portion, barrel portion and working head portion.

With reference to FIG. 1 it is shown a general view of a device 10 according to the present invention. The device comprises the following main parts: a handle portion 12, a barrel portion 14 and a working head portion 16. The length of the barrel portion and of the working head portion is selected in such a manner that the working head portion can be easily brought to a location within a body passage, e.g. a vessel where a tubular medical accessory, e.g. stent-graft has been already brought, for example in the course of the endo-vascular prosthesis procedure, and now it should be affixed to the vessel wall. In practice the stent-graft is a tubular device made of biologically compatible plastic material and having length up to 20 cm and outside diameter of 20-40 mm.

The handle portion consists of a lower handle 18 and an upper handle 20. The handles are configured and dimensioned to enable convenient gripping by operators hand and upon pressing easy bringing the upper handle close to the lower handle. The upper handle is hingeably mounted with respect to the lower handle such that upon pressing or release it can pivot around an axle 22. The handle portion comprises also a safety guard 24, which can swivel around an axle 26 from an upright position, which is shown in FIG. 1 to a horizontal position. The safety guard can be locked in the upright position by virtue of a groove made in the upper handle. A return spring 28 is provided, which urges the safety guard to return into horizontal position as soon as the safety guard is released from the groove. When the safety guard is brought in the horizontal position the upper handle is unlocked and it can be pressed by operator's hand towards the lower handle.

The barrel portion comprises a tubular housing 30 with extending therealong a pushing rod 32. The pushing rod can be made of a plastic material to allow its bending. The proximal extremity of the pushing rod carries a bias spring 34 while the distal extremity of the pushing rod terminates by a pusher head 36. The elements 34, 36 are seen in FIG. 2.

The upper handle is provided with a lever end 38, which contacts the proximal end of the pushing rod such that in order to bring the upper handle closer to the lower handle one should overcome resistance of the bias spring. It can be readily appreciated that upon bringing the upper handle closer to the lower handle the lever end 38 pushes on the proximal extremity of the rod to protract it distally while overcoming resistance of the bias spring. On the other hand upon release of the upper handle the bias spring will force the pushing rod to retract proximally.

The distal end of the housing 30 is coupled to the working head portion by a hinge joint, which comprises a bushing 40 connected to the proximal end of the working head portion and embracing a spherical neck 41 provided at the distal end of the housing. By virtue of this provision the working head portion can be displaced at a desirable angle in any plane with respect to the barrel portion. The advantage of this arrangement will be explained further with reference to FIG. 6.

Figure 2:
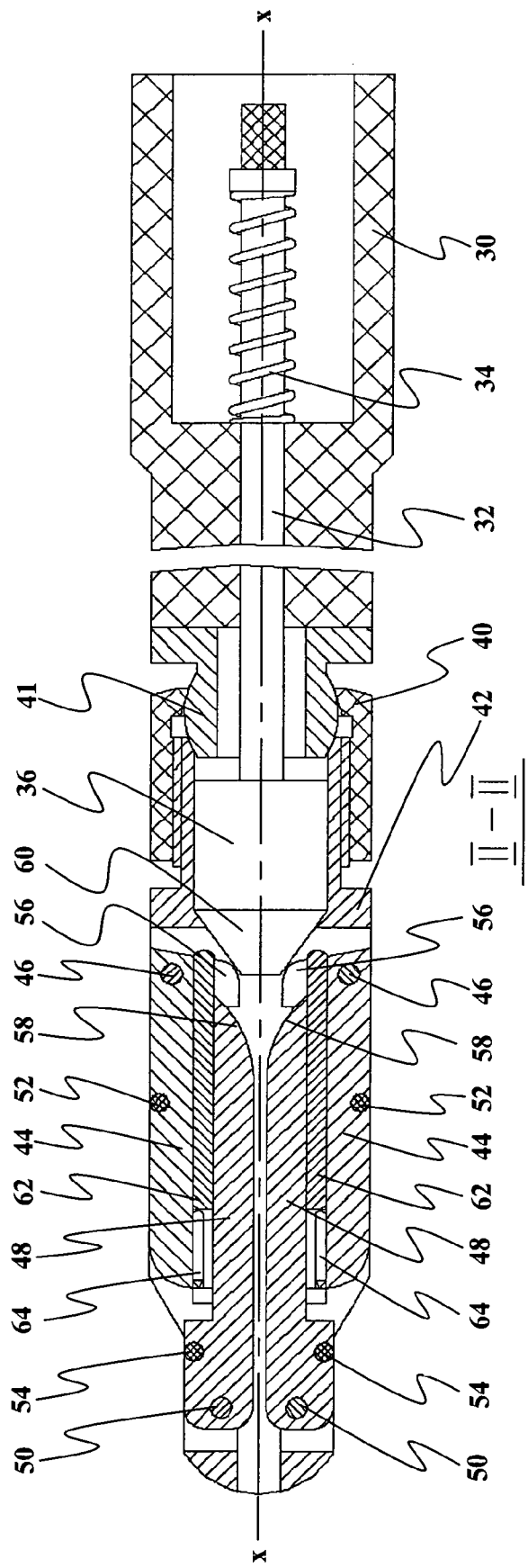
FIG. 2 is cross-sectional view of FIG. 1 taken along section II-II.

Referring to FIG. 2 it is seen that the working head portion comprises a main body portion 42, in which is deployed a plurality of swiveling wings 44 mounted with possibility to swivel about respective axles 46. In FIG. 2 two of the wings are seen. In practice the amount of wings is three and they are symmetrically arranged around the main body portion at 120 degrees. A distal end of the main body portion is fitted with a plurality of swiveling levers 48 mounted with possibility to swivel about their respective axles 50. The amount of swiveling levers corresponds to the amount of swiveling wings and the levers are symmetrically arranged at the circumference of the main body portion such that each lever corresponds to respective wing and there are provided three couples of wings and levers. The length of the wings and levers is selected depending on the inside diameter of the stent-graft to be affixed to the vessel wall. On a circumferential surface of the swiveling wings and levers are made annular grooves in which are deployed elastic rings 52,54. By virtue of this provision the wings and levers can be received in the main body portion being directed parallel to a longitudinal axis X-X of the device when it is not in use yet, or when it is being evacuated upon affixing the stent-graft.

It can be seen also in FIG. 2 that proximal ends 56 of the wings as well as proximal ends 58 of the levers are curved while distal end of the pusher head 36 has a conical portion 60. By virtue of this provision the wings and levers can be swiveled around their respective axles upon actuating the handle portion and protracting or retracting the pusher rod along the housing 30, depending whether the upper handle is brought close to the lower handle or released.

Extending along each wing a through going groove 66 is provided, which has rectangular cross-section. A separator plate 62 is deployed within each groove with possibility for linear displacement along the groove. Two such separator plates are seen in FIG. 2. The groove having rectangular cross-section is not seen in FIG. 2 but is shown in FIG. 3e.

It is also not seen but will be further explained with reference to FIGS. 3a and 3b that the groove is configured at its one end with a flaring exit in which a staple 64 is loaded, such that each wing carries its own staple and the working head portion is preloaded with a plurality of staples carried by the wings.

Now with reference to FIGS. 3a-f it will be explained how the staples are retained on the wings until they are forcibly displaced therefrom by swiveling levers. Despite the explanation refers to one couple of wing and lever one should appreciate that it is applicable to all three couples.

In FIG. 3a is shown top view of the wing 44 with the groove 66 extending therealong. The groove has rectangular cross-sectional configuration as shown in FIG. 3e. A flaring exit 68 having an ascending bridge portion 70 is provided at one end of the groove as seen in FIG. 3a. The exit is divided by the ascending bridge portion on a left exit and a right exit. Referring now to FIG. 3b it is seen that a U-shaped staple 64 is deployed near the flaring exit such that open ends of the staple become bent left and right as the staple passes the exit. One should appreciate that in FIG. 3b is shown a situation when the staple is on its way out of the groove. In an initial state the staple is retained in the groove adjacent to the flaring exit and is not bent yet.

In FIGS. 3c and 3d is seen that in an assembled state the wing and the groove is covered by a plank 72, which middle portion is connected to the wing by a plurality of screws 74. The remaining portion 76 of the plank is not connected to the wing. The thickness of the remaining portion is less then of the middle portion. The remaining portion covers the groove and can be resiliently bent outwardly. The remaining portion slightly presses the staple towards the wing and by virtue of this provision the staple is retained in place.

In FIG. 3f is shown a situation when the staple 64 has been forcibly pushed out of the groove towards the flaring exit. It is seen that on its way out the staple passes the ascending bridging portion, which causes resilient bending of the remaining portion outwardly such that it does not retain the staple and allows its free exit from the groove. It is not shown in FIGS. 3a-f but will be explained further with reference to FIGS. 4-5 that the staples are displaced along the grooves due to swiveling motion of the levers.

Figure 5:
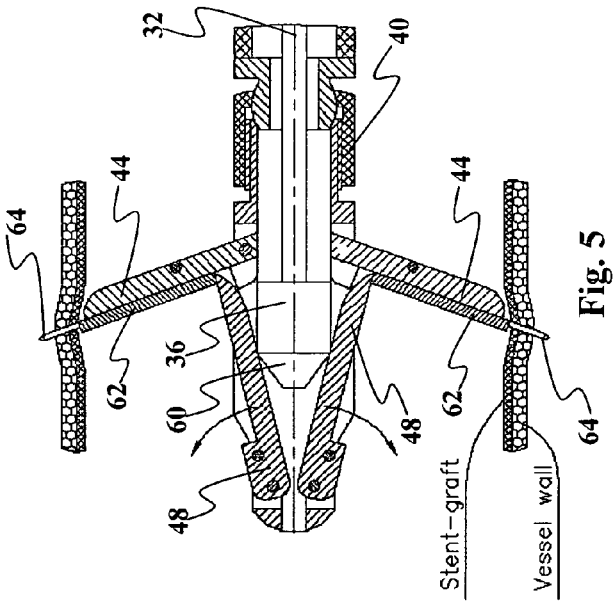
FIG. 5s is cross-sectional view of the working head portion showing the swiveling levers urging the staples to protrude from the swiveling wings and to pierce the vessel.

Now with reference to FIGS. 4-6 the operating principle of the device of the present invention will be explained in more details. One should appreciate that in operation the barrel portion of the device should be inserted via an opening in the body to bring the working head portion to a location in the body passage or cavity where the stent-graft should be affixed. The stent-graft can be brought in the body passage either before insertion of the barrel portion or by the barrel portion itself. This can be accomplished by putting the stent-graft over the barrel portion. The elastic properties of the graft material should ensure that when the graft is put on the barrel portion it adjoins it without however causing pressure on it. The barrel portion can be inserted e.g. during laparoscopic procedure or via an incision made in the femoral artery.

Figure 4:
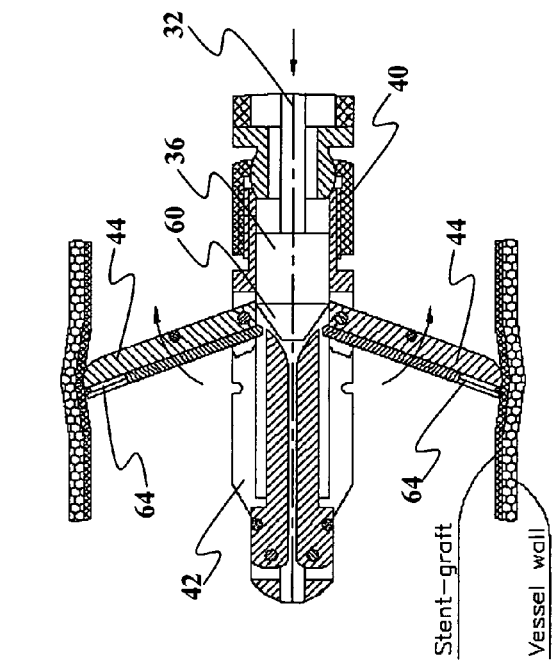
FIG. 4 is cross-sectional view of the working head portion showing the swiveling wings stretching the stent-graft in a radial direction

In FIG. 4 is shown the working head after the safety guard has been brought in the unlocked position. The upper handle has been brought close to the lower handle and the pushing rod has been protracted distally. In the end of the protracting stroke conical part 60 of the pushing head 36 contacted the curved ends of the wings and urged them to swivel towards the vessel wall in anti clockwise direction shown by arrow such that the wings were brought in a final position shown in FIG. 4. The length of the swiveling wings is selected in such a manner that when the wings are swiveled into the final position their forward most extremities abut the stent-graft wall. Seeing that both the stent-graft and the vessel have some degree of elasticity the wings stretch the stent-graft wall in radial direction together with the vessel wall. By virtue of this provision the stent-graft wall is reliably supported and now staples 64 can be protruded towards the stent-graft so as to affix it to the vessel wall. At this end the operators brings the upper handle even closer to the lower handle. As seen in FIG. 5 this action would be associated with further protracting of the conical part 60 such that it contacts curved ends 58 of the levers 48 and causes swiveling of the levers in clockwise direction shown by arrow. During the swiveling motion the forward most ends of the levers displace the separator plates 62 along their respective grooves towards the staples and eventually urge the staples to exit from the grooves while passing the flaring exits. It is seen in FIG. 5 that in the end of the protracting stroke the levers have been swiveled in such extent that the staples pierce both the stent-graft wall and the vessel wall thus providing affixing of the stent-graft to the vessel. The piercing is easy and fast since the stent-graft and the vessel are stretched in the radial direction by the wings. While passing the flaring exits the staples become slightly bent such that they can not be released from the vessel wall after piercing. By virtue of this provision the stent-graft is reliably affixed to the vessel wall and radial forces associated with pulsating blood stream will not be able to disconnect it from the vessel. Before the staples leave the wings they pass the ascending bridge portion and urge the free parts of the resilient planks to bent outwardly such that the staples are not retained any more in the grooves by the planks and their free exit is possible.

Now the handles can be released to let the pushing rod to retract in the initial position by action of the bias spring 34. The wings and the levers are returned in their initial non-swiveled position by elastic rings 52, 54. The whole device can be evacuated from the vessel and discarded.

Figure 6:
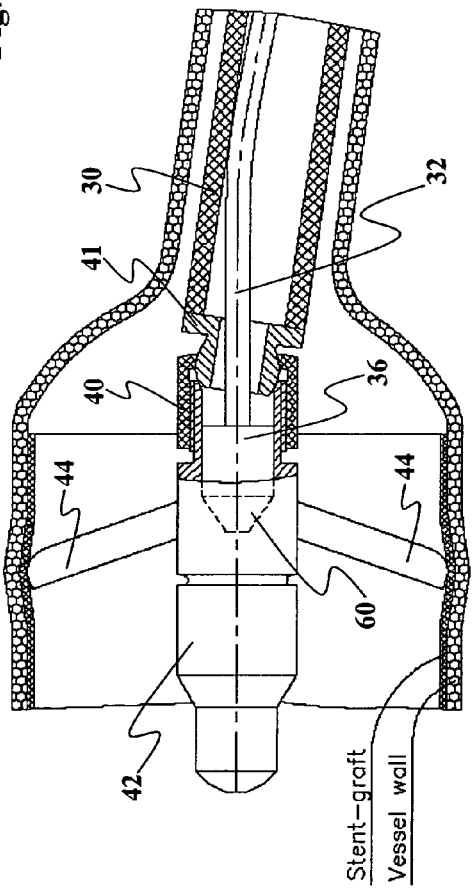
FIG. 6 is an embodiment of the device in which the working head portion is hingeably connected to the barrel portion provide possibility for relative angular displacement of the working head portion with respect to the barrel portion.

With reference to FIG. 6 it is shown the main body portion 42 being angularly displaced with respect to the barrel portion, while the pushing rod is bent. This possibility is provided by a hinge joint, comprising the bushing 40 embracing the spherical neck 41. By virtue of the hinge joint and bendable pushing rod the working head portion can be introduced within a vessel of a larger diameter through a vessel of a smaller diameter. This situation might take place when stent-graft is introduced in aorta through peripheral vessels for treatment of abdominal aortic aneurysm.

Thus by virtue of the present invention it is possible by a single "shot" to quickly and reliably affix medical accessory, e.g. stent-graft to the body passage. The affixing is possible by bringing the working head to the required location through peripheral vessels. This can be accomplished in the course of a surgical operation, which is not associated with opening cavities surrounding the body passage.

It should be appreciated that features disclosed in the foregoing description, and/or in the foregoing drawings and/or following claims both separately and in any combination thereof, be material for realizing the present invention in diverse forms thereof.

When used in the following claims, the terms "comprise", "include", "have" and their conjugates mean "including but not limited to".

As used herein, the term "medical accessory" refers to any accessory intended for placement and securing in a body of a human or an animal patient. Non-limiting examples of such medical accessories are stent-grafts, trans catheter heart valves, aortic heart valves, etc.

As used herein, the term "tubular" refers to the form of a cylinder or tube having circular or non-circular cross-section.

As used herein, the term "body passage" and the term "body cavity" refers to any hollow vessel or duct or cavity available in a body. Non-limiting examples of such passage are arteries, veins, intestines, etc.

As used herein, the term "affixing" refers to physical attachment of one object to another.

The scope of the invention is defined by the appended claims.

The invention claimed is:

1. A device for affixing a tubular medical accessory to a wall of a body passage, said device comprises a handle portion, a barrel portion and a working head portion, said barrel portion is fitted with a pushing rod, which is displaceable along the barrel portion upon actuating the handle portion, wherein said working head portion is fitted with a plurality of wings and levers and said wings are preloaded with a plurality of staples, the arrangement being such that initial displacement of the pushing rod in a distal direction the wings towards the medical accessory without swiveling the levers wherein said wings are defined by a length which is sufficient to cause stretching of the medical accessory and the body passage in a radial direction resulting in abutment of the medical accessory while still further displacement of the pushing rod in the distal direction swivels the levers causing the staples to exit from the wings such that the staples pierce the accessory and the wall of the body passage and affix the accessory to the body passage.

2. The device as defined in claim 1, in which said accessory is a stent-graft and said hollow body passage is an artery.

3. The device as defined in claim 2, in which said artery is aorta.

4. The device as defined in claim 1, in which said working head portion comprises a main body portion, in which are received the wings and levers being retained in a non-swiveled position by elastic rings.

5. The device as defined in claim 1, in which said wings and levers can be swiveled in opposite directions.

6. The device as defined in claim 1, in which said barrel portion is provided with a bias spring which urges the pushing rod to retract in a proximal direction.

7. The device as defined in claim 1, in which said barrel portion is connected to the working head portion by a hinge joint.

8. The device as defined in claim 1, in which each of the wings carries a staple.

9. The device as defined in claim 8, in which each of the wings is provided with a groove, in which is loaded the staple and one end of said groove terminates by a flaring exit such that when the staple exits from the groove it passes the flaring exit and its ends are bent.

10. The device as defined in claim 9, in which within each groove is located a separator plate, which is displaceable along the groove upon swiveling of the lever such that the separator plate urges the staple to exit from the groove towards the medical accessory.

11. The device as defined in claim 9, in which said flaring exit is divided by an ascending bridging portion.

12. The device as defined in claim 10, in which said groove and said separator plate is covered by a plank, while a portion of said plank is connected to the wing and a remaining portion of the plank is not connected.

13. The device as defined in claim 1, in which said pushing rod is provided with a conical end and each of said wings and levers is provided with a round end and upon protracting of the pushing rod in the distal direction said conical end consecutively actuates the respective wing and lever causing them to swivel.

* * * * *